United States Patent
Pauly et al.

(12) 
(10) Patent No.: US 6,599,537 B1
(45) Date of Patent: Jul. 29, 2003

(54) USE OF AT LEAST ONE EXTRACT OF A PLANT OF THE GENUS LANNEA IN A COSMETIC OR DERMOPHARMACEUTICAL COMPOSITION

(75) Inventors: Gilles Pauly, Nancy (FR); Philippe Moser, Essey les Nancy (FR); Louis Danoux, Saulxures les Nancy (FR)

(73) Assignee: Cognis France S.A., Saint-Martory (FR)

( * ) Notice: Subject to any disclaimer, the term of this patent is extended or adjusted under 35 U.S.C. 154(b) by 0 days.

(21) Appl. No.: 10/031,720

(22) PCT Filed: Jul. 13, 2000

(86) PCT No.: PCT/EP00/06696

§ 371 (c)(1),
(2), (4) Date: Apr. 17, 2002

(87) PCT Pub. No.: WO01/05368

PCT Pub. Date: Jan. 25, 2001

(30) Foreign Application Priority Data

Jul. 19, 1999 (FR) .............................................. 99 09428

(51) Int. Cl.⁷ .............................................. A61K 35/78
(52) U.S. Cl. ...................................... 424/725; 424/401
(58) Field of Search ................................. 424/725, 401

(56) References Cited

FOREIGN PATENT DOCUMENTS

JP 07010765 1/1995

OTHER PUBLICATIONS

The Wealth of India, 1962, vol. VI, Council of Scientific and Industrial Research, New Delhi, pp. 27–29.*

Singh et al., "Anti–inflammatory Activity of *Lannea coromandelica* Bark Extract in Rats", pp. 311–313, vol. 8, Phytotherapy Research, (1994).

Gandhidasan et al,. "Anti–inflammatory Action of *Lannea Coromandelica* by HRBC Membrane Stablization", pp. 81–83, vol. 62, Fitoterapia, (1991).

Chemical Abstracts, p. 372, vol. 122, No. 15, Columbus OH, 1995.

Groweiss et al., "Novel Cytotoxic, Alkylated Hydroquinones from *Lannea welwitschii*", pp. 116–121, vol. 60, No. 2, Journal of Natural Products, (1997).

* cited by examiner

*Primary Examiner*—Francisco Prats
*Assistant Examiner*—Susan D Coe
(74) *Attorney, Agent, or Firm*—John E. Drach; Steven J. Trzaska

(57) ABSTRACT

A cosmetic composition containing at least one plant extract from a plant belonging to a genus selected from the group consisting of Lannea, Odina, and mixtures thereof, for application onto a human substrate selected from the group consisting of skin, mucous membranes and epithelial appendages.

12 Claims, 1 Drawing Sheet

USE OF AT LEAST ONE EXTRACT OF A PLANT OF THE GENUS LANNEA IN A COSMETIC OR DERMOPHARMACEUTICAL COMPOSITION

BACKGROUND OF THE INVENTION

This invention relates generally to the field of cosmetics and pharmacology and more particularly to the use of at least one extract of a plant belonging to the genus Lannea, preferably *Lannea coromandelica* or *Lannea grandis,* in cosmetic or dermopharmaceutical preparations.

*Lannea coromandelica* (Houtt.) Merr. is a tree originating from the Anacardiaceae family which is encountered mainly in India and in various Asiatic countries.

In the books of traditional Indian medicine, it is sometimes confused with *Lannea grandis* because, in many works, both have the same synonym Odina woodier roxb.

The bark is traditionally used in particular in the treatment of cuts, other wounds, bruises (sprains and strains) and diarrhoea, aqueous extracts of the bark also being used as an abortive.

The leaves like the bark are also used as curatives, particularly in the treatment of inflammation, arthritis, bruises and, generally, physical pain.

It is known that an ethanol extract of *Lannea coromandelica* leaves has a protective effect on the membrane of the red blood cells against hypotonic stress which has been taken as an indication of anti-inflammatory activity (cf. Gandhidasan R. et al., Fitoterapia, 62/1, 81–83, 1991).

In addition, an ethanol-containing extract of the bark, after intraperitoneal administration, has been shown to have quite considerable anti-inflammatory activity in doses dependent upon the particular type of inflammation, this extract having no pain-killing (analgesic) or antipyretic activity (cf. Singh S. and Singh G. B., Phytotherapy Research, 8/5, 311–313,1994).

By contrast, the inventors have found that, besides the therapeutic properties mentioned above, extracts obtained from various parts of the plant also have significant biological properties so that they may be directly used in cosmetic and dermopharmaceutical compositions or for the preparation thereof.

The effects and properties demonstrated so unexpectedly and surprisingly consist in antiradical-like, cytophotoprotective, tyrosinase- and melanogenesis (depigmenting)-inhibiting and antiprotease (antielastase, anticollagenase) effects.

BRIEF SUMMARY OF THE INVENTION

Accordingly, the problem addressed by the present invention was in particular to use at least one extract of a plant belonging to the botanical genus Lannea, preferably *Lannea coromandelica* or *Lannea grandis* (synonym Odina woodier), as an active principle for the preparation of a cosmetic product for external use for the skin, the mucous membranes and/or the epithelial appendage (superficial body growth), the extract or extract mixture in question being usable on its own or together with at least one other active principle.

DETAILED DESCRIPTION OF THE INVENTION

Figure 1:
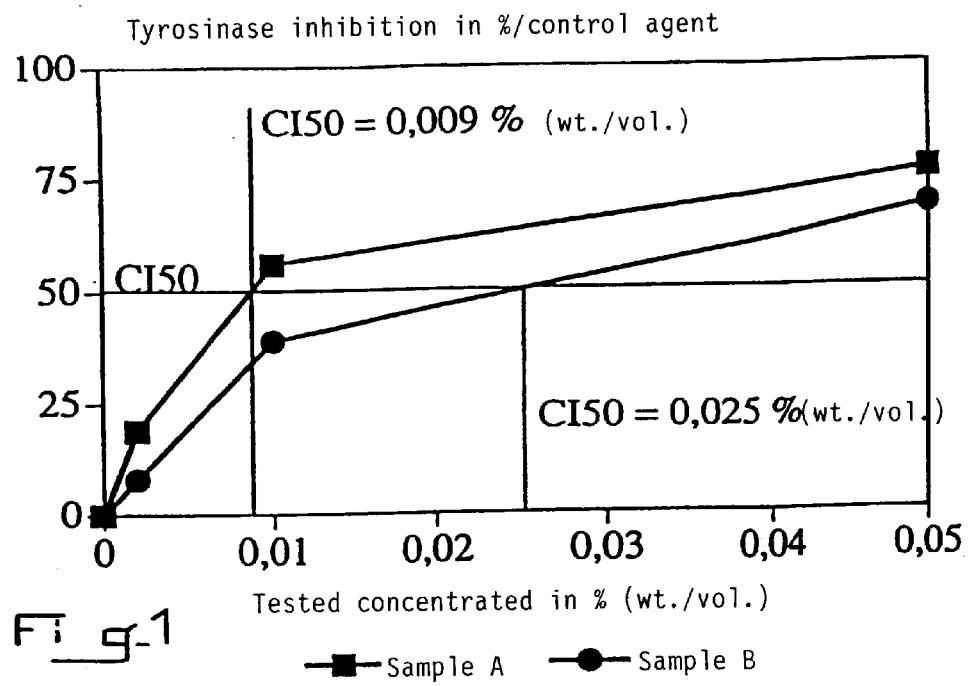
FIG. 1 is a line graph comparing the tyrosinase inhibition of the present invention versus that of a control group.

By virtue of their many effects described hereinafter, these extracts may advantageously be used on their own or together with other active ingredients in products which are intended to counteract ageing of the skin, cutaneous hyperpigmentation, pigment spots, loss of cutaneous elasticity, wrinkles, irritation and inflammation (treatment of sensitive skin types), environmental pollution and/or harm caused by the sun.

After picking and drying, the relevant parts of the plant are subjected to an extraction process for which the solvent used is advantageously selected from the group consisting of water, alcohols, ketones, esters, chlorinated solvents, polyols or mixtures of at least two of the above-mentioned solvents miscible with one another.

Alternatively, the extracts according to the present invention may also be obtained by the extraction with supercritical $CO_2$ alone or with a co-solvent or by a solvent extraction process based on microwave radiation.

In one particular embodiment of the invention, the plant extract may also consist of one or more isolated purified fraction(s), particularly by chromatography starting from a crude extract.

Various examples of procedures preferably followed for the preparation of extracts from the plants mentioned above are described in the following in order to illustrate the invention without limiting it in any way.

The parts of the plants used in the description of the examples are mentioned purely by way of example, the extracts according to the invention being obtainable from all accessible parts of the plants, i.e. the roots, bark (from the roots, stalks and the trunk), the leaves and the leaved stalks, the seeds, fruit and blossoms, but preferably from the bark of the trunk and/or the leaves.

EXAMPLE 1

Bark of the *Lannea coromandelica* strain is coarse-crushed and then fine-crushed in a blade crusher.

3 Liters of distilled water are poured into a stirrer-equipped reactor and the following steps are then successively carried out:

introduce 300 g coarse-ground bark into the reactor, extract by boiling for 1 hour with stirring, allow to cool to room temperature, separate insoluble material by centrifuging or filtering, filter the liquid extract to a porosity of ca. 0.45 µm, collect the filtrate and remove water by spraying (atomizing).

The extract obtained based on the extracted dry matter comprises 14% in relation to the coarse-ground bark.

EXAMPLE 2

3 Liters of 80% methyl alcohol are poured into a stirrer-equipped reactor and the following steps are then successively carried out:

introduce 300 g dried coarse-ground *Lannea coromandelica* leaves into the reactor, extract by heating (under reflux) for 1 hour with stirring,
allow to cool to room temperature,
filter and rinse the residue with 300 ml 80% methanol,
mix the filtrates and then clarify them by filtering to a porosity of ca. 0.45 μm,
evaporate the methanol phase in vacuo,
if necessary, remove water from the aqueous solution formed by any of the usual methods familiar to the expert in this field.

The extract obtained based on the extracted dry matter comprises 10.3% in relation to the coarse-ground leaves.

EXAMPLE 3

3 Liters of absolute ethanol are poured into a stirrer-equipped reactor and the following steps are then successively carried out:
introduce 300 g coarse-ground roots of the bark of the *Lannea coromandelica* strain into the reactor,
extract by heating (under reflux) for 1 hour with stirring,
allow to cool to room temperature,
filter and rinse the residue with 300 ml ethanol at 96°,
mix the filtrates and filter to a porosity of ca. 0.45 μm,
evaporate the ethanol phase in vacuo at 40° C.,
remove traces of the sol vent by drying the extracts in a ventilated drying oven at 40–50° C.

The extract obtained comprises 16.1% in relation to the coarse-ground bark.

The following Table is a list—intended for information—of all the *Lannea coromandelica* extracts which the inventors obtained by steps similar to those described above.

| Extracted part of the plant | Extract type | Yield in % |
| --- | --- | --- |
| Bark of the trunk, sample A | Aqueous extract | 13.9 |
| | 80% Methanol extract | 18.7 |
| | Ethanol extract | 16.1 |
| Bark of the trunk, sample B | Aqueous extract | 11.9 |
| | 80% Methanol extract | 14.1 |
| | Ethanol extract | 14.1 |
| Leaves | Aqueous extract | 10.2 |
| | 80% Methanol extract | 10.3 |
| | Ethanol extract | 12.1 |

I) Demonstration of Inhibition of Melanogenesis by *Lannea coromandelica* Extracts a) Principle of the Tests Melanin, a biological polymer which determines the color of the skin, is produced in epidermal melanocytes by a specific enzyme, tyrosinase. This enzyme catalyzes the first two stages in the synthesis of melanin, i.e. the conversion of the tyrosine into DOPA (dihydroxy phenyl alanine) and then into dopachromium. The dopachromium is then oxidized under the effect of other enzymes and polymerized into melanin which is passed onto the keratinocytes in the form of small granules, the melanosomes.

In addition, it has been found that ageing under the effect of light can cause the appearance of dark unattractive spots which are produced by hyperactivity of the melanocytes.

The ability of Lannea extracts, particularly *Lannea coromandelica* extracts, to reduce the activity of the melanocytes has been evaluated by a tyrosinase inhibition test in tubo and by a melanogenesis inhibition test in vitro, of which the principles are summarized below:

In Tubo Tyrosinase Inhibition Test
mixing of the L-DOPA with tyrosinase and the *Lannea coromandelica* extracts to be tested,
recording of the DO at 475 nm of the dopachromium,
calculation of the kinetics, then the CI50 (extract concentration which produces a 50% inhibition of the enzyme activity).

In vitro Melanogenesis Inhibition Test on B16 Melanocytes
inoculation of the melanocytes into a growth substrate,
incubation for three days at 37° C., $CO_2$=5%,
introduction of the *Lannea coromandelica* extracts into a medium which activates melanogenesis,
incubation for three days at 37° C., $CO_2$=5%,
spectrophotometric dosing of the proteins (co-called Bradford method) and the melanin (DO at 475 nm) into the homogenized melanocytes,
calculation of an activity index which corresponds to the ratio (protein level/melanin level) for an optimal dose of extract.

It follows that the higher the index (>1), the greater the ability to inhibit melanogensis.

b) Results

FIG. 1 of the accompanying drawings is characteristic of the results obtained (in tubo tyrosinase inhibition test using aqueous extracts of the *Lannea coromandelica* bark). All the results (CI50 value) are set out in Table 1 below.

TABLE 1 in tubo tyrosinase inhibition by *Lannea coromandelica* extracts: values = C150 in % by wt./vol. (weight/volume)

| Extracted parts | Trunk bark | | |
| --- | --- | --- | --- |
| CI50 in % by wt./vol. | Sample A | Sample B | Leaves |
| Aqueous extract | 0.009% | 0.025% | 0.093% |
| Methanol extr. 80% | 0.009% | 0.007% | 0.05% |
| Ethanol extract 96° | 0.008% | 0.007% | 0.130% |
| Hydroquinone | CI50 = 0.025% by wt./vol. | | |

Figure 2:
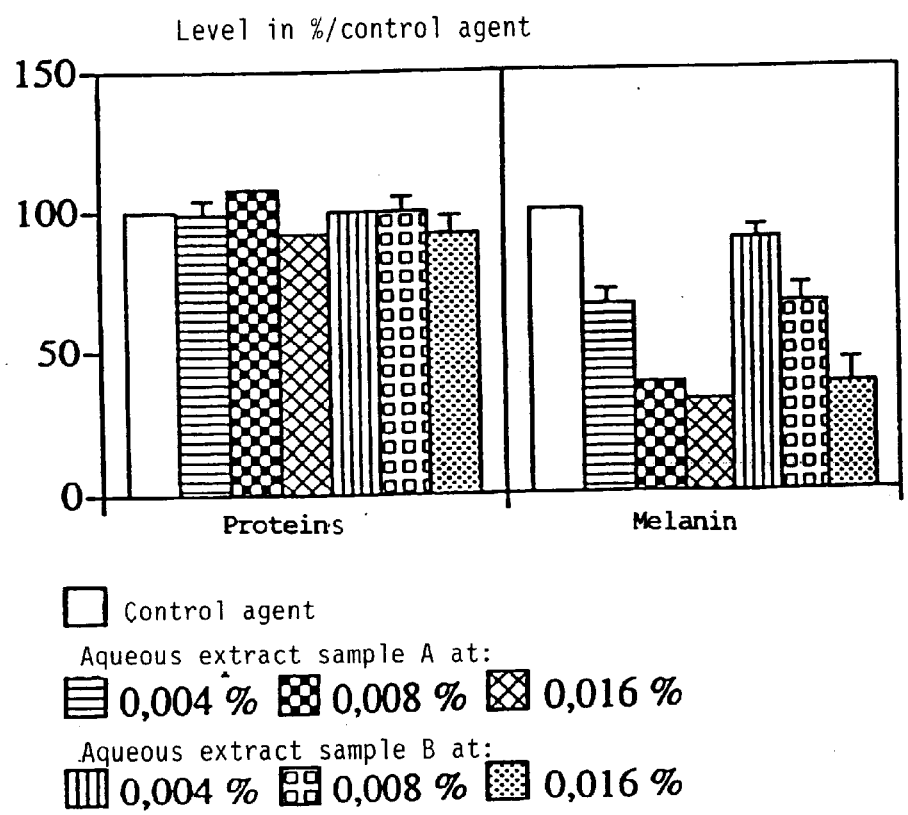
FIG. 2 is a bar graph comparing the effects of protein and melanin inhibition of composition in accordance with the present invention, at varying active levels, versus that of a control group.

FIG. 2 of the accompanying drawings (statistical results: average±typical deviation, two tests, repeated three times) is characteristic of the results obtained on B16 melanocyte. All the results obtained by tests similar to those shown in FIG. 2 are set out in Table II.

TABLE II

In vitro melanogenesis inhibition on B16 melanocytes by aqueous extracts of the bark of *Lannea coromandelica*. Values shown: I = activity index on B16 melanocytes.

| | Tested | Trunk bark | |
| --- | --- | --- | --- |
| Extracted parts | dose % by wt./vol. | Sample A | Sample B |
| Aqueous extract | 0.016 | I = 2.9 | I = 2.5 |
| Methanol extract 80% | 0.032 | I = 2 | I = 2.5 |
| Ethanol extract | 0.016 | I = 2.6 | I = 2.4 |
| Arbutin | I = 3.14 (for the 0.3% dose) | | |

The results of these two test series show that the *Lannea coromandelica* extracts according to the invention have considerable melanogenesis inhibition capacities; these capacities are at least partly attributable to inhibition of tyrosinase.

This property enables the extracts to be used in the local treatment of cutaneous hyperpigmentations such as, for example, age pigment spots.

II) Demonstration of the Anti-free Radical Properties of the *Lannea coromandelica* Extracts Free radicals (RLs) are activated chemical species characterized by the presence of a free electron which is not bound in pairs. They can be formed from endogenous molecules such as, for example, unsaturated lipids, certain amino acids or from oxygen during spontaneous enzymatic reactions of the general metabolism or which were induced during inflammation. Certain stress factors such as, for example, UV rays or environmental pollution also promote their formation and any excess of free radicals causes damage to all constituents of living tissue (lipids, proteins, sugars, ADN, etc.). This toxicity of free radicals is greatly potentialized by the presence of oxygen and explains the ageing of the living organisms or even serious pathologies, such as skin cancer.

The anti-free radical properties of *Lannea coromandelica* extracts are evaluated by in tubo chemical and biochemical tests which relate both to the original radical-like forms and to the reactive oxygen-induced forms. These tests are carried out on synthetic substrates and also on a natural substrate, collagen, the dermal glycoprotein which is highly sensitive to the activity of the reactive forms of oxygen (or FRO).

These tests are completed by a test for human fibroblasts in an in vitro culture which evaluates the cytophotoprotective effects of *Lannea coromandelica* extracts on the cells against UV-A.

UV-As are selected as a study model because they penetrate into the inner skin and introduce an oxidizing stress into the skin which is reflected in particular in a lipoperoxidation of the cytoplasmic membrane. The lipoperoxides formed split up into malonaldialdehydes which are responsible for the crosslinking of numerous biological molecules, such as proteins for example (enzyme inhibition), and nuclein bases (mutagenesis).

a) DPPH° Test

DPPH (diphenyl picryl hydrazyl) is a stable, free, violet-colored radical which is modified in its leuco compound by the substances that trap the free radicals (=scavenger or bait effect).

The result is expressed in leuco compound levels which are formed in the presence of the active agent (in % in relation to the control with no active principle).

The results are set out in Table III below.

TABLE III

Anti-radical effect of *Lannea coromandelica* extracts. Anti-DPPH° test: level of leuco compound formed (in % in relation to the control: average of 2 tests).

| Dose in % (wt./vol.) | Aqueous bark extract Sample A | 80% methanol bark extract Sample A | Ethanol bark extract Sample A | Ascorbic acid |
|---|---|---|---|---|
| Control | 0 | 0 | 0 | 0 |
| 0.0003% extract | 27 | 34 | 31 | |
| 0.001% extract | 73 | 90 | 86 | 49 |
| 0.01% extract | 93 | 93 | 93 | 75 |
| CI50 in % (wt./vol.) | 0.0007 | 0.0005 | 0.0005 | 0.0013 | b) Anti-hydroxyl Radical Test (HO°)

Anti-HO°—Test with Deoxyribose (Fenton Reaction)

These tests evaluate the ability of an active substance to eliminate ("bait") HO° produced by the Fenton reaction ($H_2O_2$ in the presence of iron).

HO° can be exposed by deoxyribose. Deoxyribose is an essential compound of ADN which is oxidized and then fragmented by HO°. The oxidation product of deoxyribose is exposed by condensation with thiobarbituric acid (measurement of optical density at 532 nm). This test is carried out with and without EDTA in order to determine the ability of the extract to form active complex compounds with iron ("Ferriprive effect").

The results are set out in Tables IV.1) and IV.2) below and demonstrate the anti-HO° effect of the *Lannea coromandelica* extracts. Tests with deoxyribose (Fenton reaction) (results in percentage inhibition of the hydroxylation rate: average of 2 tests).

IV.1) "Fenton" reaction with EDTA

| Dose in % (wt./vol.) | Aqueous bark extract Sample A | 80% methanol bark extract Sample A | Ethanol bark extract Sample A | Ascorbic acid |
|---|---|---|---|---|
| Control | 0 | 0 | 0 | 0 |
| 0.03% extract | 0 | 0 | 3 | |
| 0.1% extract | 29 | 25 | 23 | 45 |
| 1% extract | | | | 73 |
| CI50 in % (wt./vol.) | >0.1 | >0.1 | >0.1 | 0.26 |

IV.2) "Fenton" reaction without EDTA

| Dose in % (wt./vol.) | Aqueous bark extract Sample A | 80% methanol bark extract Sample A | Ethanol bark extract Sample A | Ascorbic acid |
|---|---|---|---|---|
| Control | 0 | 0 | 0 | 0 |
| 0.003% extract | 8 | 37 | 51 | |
| 0.01% extract | 36 | 76 | 75 | 5 |
| 0.03% extract | 78 | 79 | 77 | 75 |
| 0.1% extract | 73 | 76 | 78 | 2 |
| 1% extract | | | | 56 |
| CI50 in % (wt./vol.) | 0.017 | 0.005 | 0.003 | 0.9 | c) Biochemical or Enzymatic Tests

*Anti-anion superoxide effect ($O_2^-$)

$O_2^-$ is produced during the oxidizing stress through the introduction of an enzyme, xanthine oxidase (XOD), which degrades the excess hypoxanthine (HX) during an interruption in or disruption of the energy metabolism in living tissue.

$O_2^-$ is toxic, particularly because of its ability to form hydrogen peroxide ($H_2O_2$)—which in turn forms a source of HO° through the Fenton reaction—either spontaneously or in the presence of Superoxid-Dismutase (SOD).

The biochemical tests are carried out with HX in the presence of XOD and the $O_2^-$ are exposed by luminol or a mixture of luminol and peroxidase, which exposes $O_2^-$ and $H_2O_2$, or by a tetrazolium salt (NBT) which forms a red compound evaluated at 540 nm.

The results are set out in Tables V.1), V.2) and V.3) below which demonstrate the anti-anion superoxidase effect $O_2^-$ in tubo of the *Lannea coromandelica* extracts.

V.1) Test with luminol: results in percentage inhibition (average of 2 tests)

| Dose in % (wt./vol.) | Aqueous bark extract Sample A | 80% methanol bark extract Sample A | Ethanol bark extract Sample A | Ascorbic acid |
|---|---|---|---|---|
| Control | 0 | 0 | 0 | 0 |
| 0.0001% extract | 36 | 38 | 40 | 5 |
| 0.001% extract | 90 | 94 | 93 | 92 |

-continued

V.1) Test with luminol: results in percentage inhibition (average of 2 tests)

| Dose in % (wt./vol.) | Aqueous bark extract Sample A | 80% methanol bark extract Sample A | Ethanol bark extract Sample A | Ascorbic acid |
|---|---|---|---|---|
| 0.01% extract | 100 | 100 | 100 | 100 |
| CI50 in % (wt./vol.) | 0.0003 | 0.0003 | 0.0003 | 0.0006 |

V.2) Test with luminol + microperoxidase: results in percentage inhibition (average of 2 tests)

| Dose in % (wt./vol.) | Aqueous bark extract Sample A | 80% methanol bark extract Sample A | Ethanol bark extract Sample A | Ascorbic acid |
|---|---|---|---|---|
| Control | 0 | 0 | 0 | 0 |
| 0.001% extract | 1 | 14 | 2 | 0 |
| 0.01% extract | 98 | 100 | 99 | 94 |
| 0.03% extract | 100 | 100 | 100 | |
| CI50 in % (wt./vol.) | 0.0055 | 0.0048 | 0.0055 | 0.0058 |

V.3) Test with NBT: results in percentage inhibition (average of 2 tests)

| Dose in % (wt./vol.) | Aqueous bark extract Sample A | 80% methanol bark extract Sample A | Ethanol bark extract Sample A | Ascorbic acid |
|---|---|---|---|---|
| Control | 0 | 0 | 0 | 0 |
| 0.001% extract | 9 | 16 | 15 | |
| 0.01% extract | 58 | 64 | 65 | 15 |
| 0.03% extract | 75 | 82 | 82 | |
| 0.1% extract | 90 | 94 | 91 | 32 |
| 1% extract | | | | 65 |
| CI50 in % (wt./vol.) | 0.0085 | 0.0074 | 0.0073 | 0.5909 |

*Anti-singlet oxygen effect on type I collagen

Collagen is a dermal glycoprotein which is very sensitive to the activity of the reactive form of oxygen (or FRO). It was shown that singlet oxygen ($O_2^1$) produces troublesome crosslinkings among the proteins.

The principle of this test is based on measurement of the viscosity of an aqueous solution of type I collagen in the presence of a photochemical $O_2^1$-evolving system.

$O_2^1$, which is produced by riboflavin in the presence of UV-A, causes the collagen to gel in the presence of glucose which is reflected in an increase in viscosity. This effect is inhibited by the molecules which expose $O_2^1$, such as thiourea or aminoguanidine for example.

Viscosity is evaluated by measurement of the throughflow time through the capillary of a "Cannon Fenske" viscosimeter.

The results are set out in Table VI below which emphasizes the photoprotective effects of the *Lannea coromandelica* extracts on type I collagen (results in percentage inhibition).

TABLE VI

| Dose in % (wt./vol.) | Aqueous bark extract Sample A | 80% Methanol bark extract Sample A | Aminoguanidine |
|---|---|---|---|
| Control | 0 | 0 | 0 |
| 0.005% extract | | | 57 |
| 0.01% extract | 54 | 70 | |
| 0.015% extract | | | 75 |
| CI50 in % (wt./vol.) | 0.009 | 0.007 | 0.004 | d) Anti-UVA-cytophotoprotection Test on Human Fibroblasts

This in vitro test evaluates the ability of *Lannea coromandelica* extracts according to the invention to afford human fibroblasts cytophotoprotection against UV-A.

The UV-As are selected as a study model because they penetrate into the inner skin and introduce an oxidizing stress into the skin which is reflected in particular in a lipoperoxidation of the cytoplasmic membrane. The lipoperoxides formed split up into malonaldialdehydes (MDAS) which are responsible for the crosslinking of numerous biological molecules, such as proteins for example (enzyme inhibition), and nuclein bases (mutagenesis).

Fibroblasts are inoculated into a nutrient medium defined with calf foetus serum. The *Lannea coromandelica* extract was added 2 to 3 days after inoculation. After incubation for 2 to 3 days at 37° C./$CO_2$=5%, the nutrient medium is replaced by a salt solution and the fibroblasts are exposed to a dose of UV-A (15 J/cm$^2$).

After the exposure, the MDA level in the salt solution floating on the surface is determined and the protein level in the fibroblasts is measured. The MDA level is determined by reaction to thiobarbituric acid while the protein levels are determined by the Bradford method.

The results are set out in Tables VII.1 and VII.2 below which enable the cytophotoprotective effect of the *Lannea coromandelica* extracts on human fibroblasts to be emphasized through in vitro survival (results in % in relation to the irradiated control agent MDA) and in relation to the non-irradiated control agent (proteins): average of 1 or 2 tests carried out three times).

TABLE VII.1)

| | MDA | | | |
|---|---|---|---|---|
| Parameter evaluated Tested extracts | Aqueous bark extract Sample A | 80% Methanol bark extract Sample A | Ethanol bark extract Sample A | Vitamin E |
| Control without UV-A | 0 | 0 | 0 | 0 |
| Control with UV-A | 100 | 100 | 100 | 100 |
| 0.0003% extract | 96 | 74 | 84 | 21 |
| 0.001% extract | 64 | 56 | 59 | 8 |

TABLE VII.2)

| | Proteins | | | |
|---|---|---|---|---|
| Parameter evaluated Tested extracts | Aqueous bark extract Sample A | 80% Methanol bark extract Sample A | Ethanol bark extract Sample A | Vitamin E |
| Control without UV-A | 100 | 100 | 100 | 100 |
| Control with UV-A | 95 | 95 | 95 | 96 |
| 0.0003% extract | 100 | 96 | 97 | 97 |
| 0.001% extract | 93 | 93 | 98 | 98 |

The results of the various tests show that *Lannea coromandelica* extracts are well capable of eliminating ("baiting") free radicals, the hydroxyl radical and superoxide anions. This anti-free-radical activity is observed in the photoprotection test on type I collagen and in the cytophotoprotection test on human fibroblasts in in-vitro cultures.

This activity is at least partly attributable to a baiting (or scavenger) effect against free radicals and reactive forms of oxygen (radical hydroxyl, anion superoxide and singlet oxygen) and a chelate-binding effect of iron as demonstrated by the anti-HO° activity which is greater in the absence of EDTA than in the presence of EDTA.

These various results clearly show that *Lannea coromandelica* extracts according to the invention with their cytophotoprotective activity are suitable for use in care preparations for the skin or the epithelial appendage (superficial body growth) which are intended to control signs of ageing, environmental stress, inflammation, irritation (treatment of sensitive skin types).

III. Antiprotease Activity of the *Lannea coromandelica* Extracts

The proteases secreted by the polymorphonuclear neutrophiles (PNN) during inflammation or by fibroblasts exposed to UV-A radiation produce a decay of the proteins which structure the extracellular matrix of the inner skin. Accordingly, the PNNs secrete an elastase (serine protease) which acts on elastin, proteoglycans and collagens while "old" or irradiated fibroblasts secrete metalloproteases with elastase and collagenase activities.

The two protease types were evaluated by enzymatic in tubo reactions.

a) Antielastase Test

The in tubo tests are carried out with an elastase of the abdominal salivary gland (serine protease) using two types of substrate: a synthetic color-forming (chromogenic) substrate and a natural substrate consisting of elastin connected with Congo red.

Incubation lasts 30 minutes at room temperature and coloration is measured at 410 nm and 520 nm.

The inhibition test standard tested for comparison is 1 antitrypsin.

The results are set out in Tables VIII and IX below.

TABLE VIII

Antielastase activity of the Lannea coromandelica extracts. A method in which elastin connected with Congo red is used: results in percentage inhibition.

| Dose in % (wt./vol.) | 80% Methanol bark extract Sample A | Ethanol bark extract Sample A |
|---|---|---|
| Control | 0 | 0 |
| 0.1% extract | 0 | 0 |
| 0.2% extract | 6 | 29 |
| 0.3% extract | 35 | 100 |
| C150 in % by wt./vol. | 0.35 | 0.23 |

NB: C150 in % by wt./vol. for 1α antitrypsin = 0.04%

TABLE IX

Antielastase activity of the Lannea coromandelica extracts. A method which uses the synthetic substrate: results in percentage inhibition.

| Dose in % (wt./vol.) | Aqueous bark extract Sample A | 80% Methanol extract Sample A | Ethanol bark extract Sample A |
|---|---|---|---|
| Control | 0 | 0 | 0 |
| 0.01% extract | 0 | 22 | 37 |
| 0.01% extract | 56 | 65 | 67 |
| 0.01% extract | 66 | 76 | 77 |
| 0.01% extract | 72 | 82 | 83 |
| C150 in % by wt./vol. | 0.028 | 0.023 | 0.019 |

NB: C150 in % by wt./vol. for 1α antitrypsin = 0.04% b) In Tubo Anticollagenase Test

The tests are carried out with a clostridium hystoliticum collagenase and a synthetic chromogenic substrate: FAL-GPA. Incubation lasts 30 minutes at room temperature and optical density is measured at 324 nm. The inhibition test standard tested for comparison is cysteine.

The results are set out in Table X below which emphasizes the anticollagenase activity of the *Lannea coromandelica* extracts (results in percentage inhibition).

TABLE X

| Dose in % (wt./vol.) | Aqueous bark extract Sample A | 80% Methanol extract Sample A | Ethanol bark extract Sample A |
|---|---|---|---|
| Control | 0 | 0 | 0 |
| 0.01% extract | 46 | 0 | 2 |
| 0.03% extract | 100 | 43 | 51 |
| 0.1% extract | 100 | 100 | 100 |
| 0.3% extract | 100 | 100 | 100 |
| C150 in % by wt./vol. | 0.0111 | 0.039 | 0.030 |

NB: C150 in % by wt./vol. of cysteine = 2.4%

It is clear from the above results that *Lannea coromandelica* extracts are well capable of inhibiting elastase and collagenase.

Accordingly, extracts according to the invention may advantageously be used for various applications involving inhibition of these proteases such as, for example, tightening of the skin, controlling ageing of the skin (wrinkles) and scalp, anti-inflammatory and anti-irritation effects.

The present invention also relates to a cosmetic or dermopharmaceutical composition for external application to the skin, the mucous membranes and/or the epithelial appendage (superficial body growth) which contains at least one extract of a plant belonging to the genus Lannea, preferably *Lannea coromandelica* or *Lannea grandis,* as an active principle on its own or together with at least one other active principle used for its strong anti-radical-like effect, for its ability to inhibit tyrosinase and melanogensis, for its strong anticollagenase effect, for its strong antielastase effect and/or for its cytophotoprotective effect (particularly against UV-A).

The said extract(s) may be used in this composition to utilize one of the above-mentioned effects or properties regarded separately or at least two of these effects or properties or even for all effects or properties regarded simultaneously.

The cosmetic composition according to the invention advantageously contains between 0.001% and 20% by weight and preferably between 0.1% and 3% by weight of a plant extract or a mixture of plant extracts belonging to the genus Lannea, preferably *Lannea grandis* or *Lannea coromandelica*, as mentioned above or as obtained by any of the processes mentioned above.

In addition, the above-mentioned extracts may be used in any form of a galenic medicine as normally used in cosmetics, for example in emulsions (oil-in-water and water-in-oil), face lotions, body milk, gels, hydrogels, creams, pommades, soaps, sticks, sprays, epithelial appendage (superficial body growth) lotion and shampoos.

In addition, the said extracts or mixtures of plant extracts may be incorporated in cosmetic vectors such as, for example, liposomes, macro-, micro- and nanocapsules, macro-, micro- and nanoparticles or the like.

The following Examples illustrate various formulations of the cosmetic compositions according to the invention and their preparation.

EXAMPLE 1

A cosmetic product in the form of a leave-on lotion for treating cutaneous hyperpigmentation and pigment spots may have the following composition:

| | |
|---|---|
| 80% methanol extract of Lannea bark | 0.10 |
| distilled water | 9.50 |
| hydroxyethyl cellulose | 0.50 |
| Elestab 350 (Laboratoires Sérobiologiques) | 0.50 |
| perfume | 0.10 |
| RH 410 Cremophor | 0.30 |
| distilled water qsf | 100.00 |

The process for preparing the leave-on lotion essentially comprises dissolving the Elestab 305 and the hydroxyethyl cellulose in water heated to around 50° C., dispersing the perfume and the RH 410 Cremophor in the solution and then cooling the mixture to room temperature, dissolving the Lannea extract therein and finally filtering the whole.

EXAMPLE 2

A cosmetic product in the form of a cream for treating ageing skin, wrinkles and loss of suppleness of the skin may be made up from the following two phases:

| | |
|---|---|
| fatty phase | |
| Ceteareth 25 | 2.00 |
| Ceteareth 6 and stearyl alcohol | 1.00 |
| cetyl alcohol | 4.00 |
| glycol stearate | 4.00 |

| | |
|---|---|
| -continued | |
| petrolatum | 5.00 |
| caprylic triglycerides/caprins | 5.00 |
| aqueous phase | |
| glycerol | 10.00 |
| aqueous Lannea bark extract | 3.00 |
| distilled water | 8.50 |
| Elestab 4112 preservative (Labo. Sérobiol.) | 0.40 |
| perfume | 0.30 |
| distilled water qsf | 100.00 |

Preparation of the above-mentioned cream essentially comprises heating the fatty phase to 80° C., heating the aqueous phase to 80° C. and dissolving the Elestab 4112, separately preparing the mother solution of Lannea extract, adding the fatty phase to the aqueous phase while stirring (turbine agitator), adding the mother solution of Lannea extract at around 50° C. and finally allowing the whole to cool while stirring.

EXAMPLE 3

A cosmetic product in the form of a cream for sensitive skin types for treating skin damaged by exposure to the sun and environmental stress may be made up of the following phases:

| | |
|---|---|
| fatty phase: | |
| glycol stearate | 14.00 |
| dodecane octyl | 6.00 |
| dibutyl adipate | 6.00 |
| Ceteareth 12 | 1.50 |
| Ceteareth 20 | 1.50 |
| aqueous phase: | |
| PVP (polyvinyl pyrrolidone) | 0.50 |
| glycerol | 4.00 |
| Elestab 388 (Laboratoires Sérobiologiques) | 2.00 |
| 80% methanol extract of Lannea bark | 3.00 |
| distilled water | 9.00 |
| perfume | 0.20 |
| distilled water qsf | 100.00 |

Preparation of the above-mentioned cream essentially comprises heating the fatty phase to 80° C., heating the aqueous phase to 80° C. and dissolving the Elestab 388 and PVP, adding the fatty phase to the aqueous phase while stirring (turbine agitator) at 80° C. and, finally, gradually cooling the whole while stirring, adding the mother dispersion of the Lannea extract at around 50° C. and finally allowing the whole to cool while stirring.

The invention is not of course confined to the above Examples. Modifications may be made, particularly to the composition of the various elements or by the replacement of technical equivalents, without departing from the scope of the invention.

What is claimed is:

1. A cosmetic composition comprising at least one plant extract from a plant belonging to a genus selected from the group consisting of Lannea, Odina, and mixtures thereof for application onto a human substrate selected from the group consisting of skin, mucous membranes and epithelial appendages, wherein the plant extract is obtained using a solvent selected from the group consisting of methanol, ethanol, a combination of water and methanol, a combination of water and ethanol, and mixtures thereof.

2. The composition of claim 1 wherein the plant extract is extracted from a plant selected from the group consisting of *Lannea coromandelica, Lannea grandis,* and mixtures thereof.

3. The composition of claim 1 wherein the plant extract comprises at least one isolated fraction purified from an extract.

4. The composition of claim 1 further comprising an active ingredient selected from the group consisting of an anti-radical agent, a tyrosinase-inhibiting agent, a melanogenesis-inhibiting agent, an anticollagenase agent, an antielastase agent, a cytoprotective agent, and mixtures thereof.

5. The composition of claim 1 wherein the plant extract is present in the composition in an amount of from about 0.001 to 20% by weight, based on the weight of the composition.

6. The composition of claim 1 wherein the plant extract is present in the composition in an amount of from about 0.1 to 3% by weight, based on the weight of the composition.

7. A process for treating a human substrate selected from the group consisting of skin, mucous membranes and epitheleal appendages comprising contacting the substrate with a cosmetic composition containing at least one plant extract from a plant belonging to a genus selected from the group consisting of Lannea, Odina, and mixtures thereof, wherein the plant extract is obtained using a solvent selected from the group consisting of methanol, ethanol, a combination of water and methanol, a combination of water and ethanol, and mixtures thereof.

8. The process of claim 7 wherein the plant extract is extracted from a plant selected from the group consisting of *Lannea coromandelica, Lannea grandis,* and mixtures thereof.

9. The process of claim 7 wherein the plant extract comprises at least one isolated fraction purified from an extract.

10. The process of claim 7 wherein the composition further comprises an active ingredient selected from the group consisting of an anti-radical agent, a tyrosinase-inhibiting agent, a melanogenesis-inhibiting agent, an anticollagenase agent, an antielastase agent, a cytoprotective agent, and mixtures thereof.

11. The process of claim 7 wherein the plant extract is present in the composition in an amount of from about 0.001 to 20% by weight, based on the weight of the composition.

12. The process of claim 7 wherein the plant extract is present in the composition in an amount of from about 0.1 to 3% by weight, based on the weight of the composition.

* * * * *